(12) United States Patent
Au et al.

(10) Patent No.: US 8,704,670 B2
(45) Date of Patent: Apr. 22, 2014

(54) TARGET BASED SMOKE DETECTION SYSTEM

(75) Inventors: Kwong Wing Au, Bloomington, MN (US); Thomas W. Shoaff, Elburn, IL (US); Scott R. Lang, Geneva, IL (US)

(73) Assignee: Honeywell International Inc., Morristown, NJ (US)

( * ) Notice: Subject to any disclaimer, the term of this patent is extended or adjusted under 35 U.S.C. 154(b) by 589 days.

(21) Appl. No.: 12/951,717

(22) Filed: Nov. 22, 2010

(65) Prior Publication Data

US 2012/0126985 A1    May 24, 2012

(51) Int. Cl.
G08B 17/12    (2006.01)
A61B 5/11    (2006.01)

(52) U.S. Cl.
CPC .................................. A61B 5/1117 (2013.01)
USPC ........ 340/578; 340/628; 340/630; 340/693.5; 340/556; 340/557; 382/103; 382/109; 348/143; 348/162; 348/164

(58) Field of Classification Search
CPC ....................................................... A61B 5/1117
USPC .............. 340/578, 628, 630, 693.5, 556, 557; 382/103, 190; 348/143, 162, 164
See application file for complete search history.

(56) References Cited

U.S. PATENT DOCUMENTS

| 4,614,968 A * | 9/1986 | Rattman et al. ................ 348/143 |
| 7,495,767 B2 * | 2/2009 | Kim et al. ....................... 356/438 |
| 2004/0155786 A1 * | 8/2004 | Guttinger et al. ............. 340/630 |

* cited by examiner

Primary Examiner — Tai T Nguyen
(74) Attorney, Agent, or Firm — Husch Blackwell LLP

(57) ABSTRACT

A smoke detector includes processing circuitry coupled to a camera. The field-of-view of the camera contains one or more targets, each having spatial indicia thereon. At least a portion of one of the targets is coated, at least in part, by an infra-red absorbing dye. The dye produces visually discernable dark areas on the coated target(s).

9 Claims, 11 Drawing Sheets a = 8"
b = 1/3 a
c = 0.5"

a = e = 17"
d = 0.5 a
c = 1"

A LINE PROFILE CONSISTS OF DARK, BRIGHT, DARK INTENSITIES

TARGET BASED SMOKE DETECTION SYSTEM

FIELD

The invention pertains to smoke detectors. More particularly, the invention pertains to smoke detectors which process images of pre-established targets in making a determination as to presence of smoke.

BACKGROUND

Numerous commercial products are offered for smoke detection in small confined areas, such as rooms, and hallways in a house. They achieve performance according to published guidelines.

These smoke/fire detectors, however, are impractical in large areas with high ceilings, such as auditorium, theater, factory, and aircraft hangar, since these detectors are point sensors and detect smoke only in a small local vicinity to the detector. As a result, large numbers of these detectors are needed.

Installation on high ceilings is difficult. Furthermore, smoke may be dispersed and not reach the height of the ceiling to be detected. Projected and reflected beam smoke detectors, which predict the presence of smoke through measurements of the attenuation of a light beam, are possible solutions. However, in addition to having limited sensitivity, beam-based detectors require precise alignment between the source emitter and the light receiver. Hence such detectors are costly to install and maintain.

Various types of target based smoke detectors are known. Embodiments are disclosed in U.S. patent application Ser. No. 12/549,115 file on Aug. 27, 2009 entitled System and Method of Target Based Smoke Detection, assigned to the assignee hereof, and incorporated herein by reference.

Target-based smoke detection systems rely on the reduction in contrast of an observed target. Preferably the target provides areas that have crisp, sharp contrast under all operating conditions and environments. A good target design also enables the system to detect various types of smoke at different intensities. On the contrary, a poor target can cause an offset in contrast computation due to the quality of images captured by low cost cameras under low light or no light conditions rendering a degraded smoke detection performance.

DETAILED DESCRIPTION

Figure 1:
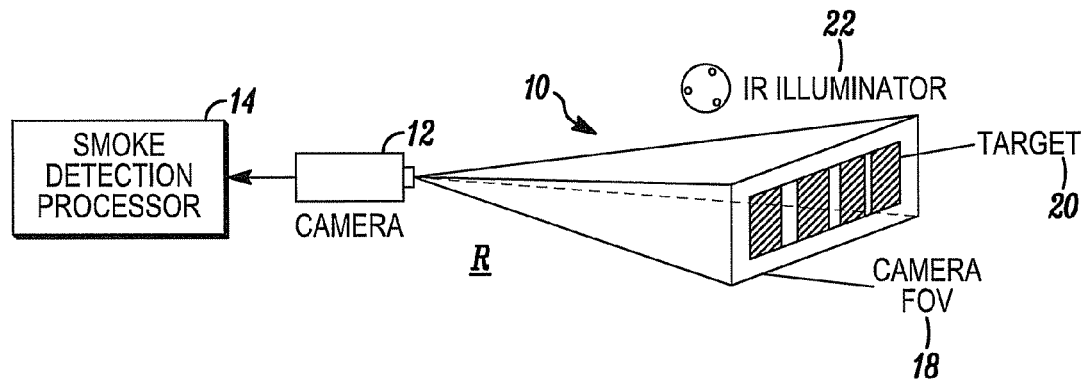
FIG. 1 is a block diagram of a system which embodies the present invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the current invention use a patterned target and a camera, such as a video camera, to detect the smoke. The patterned target is constructed to have regions negatively and/or positively responsive to infrared radiation source. Thus, regions of the target can be coated with an infrared absorbing dye and other regions can be made of infrared reflective surface. Such systems can be expected to perform better and require simple steps in installation and very minimal maintenance, thus providing a cost-effective alternate to the beam-based smoke detector.

In one aspect, a system in accordance with the invention can include a smoke detector processor, a camera, a coated, patterned, target, and optionally an illuminator preferably a near infra-red (NIR) or low power LED light. The processor, whose function is to determine whether smoke is present in the captured image, can be implemented as one of a personal computer, a digital signal processor, a programmable gate array or an application specific integrated circuit all without limitation.

In another aspect of the invention, infrared (IR) absorption dye coats the target for producing dark areas in the pattern. The desired dark areas in the pattern can be coated with different strengths of IR absorption dye. The coated areas appear as lightly tinted areas to our eyes. The same areas, however, appear dark when viewed through an IR filter. The different strengths of the IR dye produce different shades of dark. Hence, the target pattern does not become an eye-sore to the viewer and still produces a dark and bright pattern to the camera.

Because the system is working in the near infra-red domain using an IR pass filter and an IR illuminator, the visible light does not affect the smoke detection performance. That is, the system can detect smoke under room light, low light or no light conditions.

If the slightly tinted target pattern is not acceptable to a viewer, an optically opaque dye can be coated onto the target.

Hence the target will appear totally black to a viewer's eyes, but a bright and dark pattern in the near IR domain.

The camera has sufficient spatial resolution and captures images of the patterned target, which is located at a predetermined distance from the camera. The camera can respond to infra-red radiant energy emitted by a source. The target preferably contains one or more coated patterns of different spatial resolutions, for example, black and white interlaced stripes or grids of different widths. In one embodiment, a single black stripe (coated with IR absorption dye) can be bounded, at least in part by contrasting white regions. In a preferred embodiment, a single bright stripe (build with IR reflective microlens) can be bounded, at least in part by contrasting black regions.

Advantageously, in accordance with the invention, a marker or indicia can be established and stored which is indicative of location of the target. Movement of the target from the initial location can be subsequently detected. The target can be reacquired using the marker; smoke detection can continue without interruption and maintenance.

An infra-red illuminator can be used to shine (NIR) light onto the target. The illuminator is suitable for applications where smoke detection in total darkness is required.

In summary, an artistic target pattern can be formed of dark and bright areas of different shades. The dark areas of the pattern are coated with different strengths of an IR absorption dye. The bright areas of the pattern can be constructed of IR reflective surface. The target is illuminated with an IR illuminator. A camera that is fitted with an IR filter captures images of the target in near IR spectrum. The contrast reduction of the dark and bright areas in the pattern indicates the presence of smoke.

With reference to FIG. 1, a system 10, which embodies the invention, monitors a region R for smoke. A camera 12, having a field of view 18, is directed toward a test target 20. The test target 20 is mounted, spaced apart from camera 12, at a distance away, e.g., at a certain height on opposite walls of the region R being monitored.

The camera 12 can respond to visible or NIR radiant energy. The test target 20 has patterns representing one or more discrete spatial frequencies and/or continuous spectrum of the spatial frequencies, e.g., different sizes of black and white strips or squares.

A hardwired or programmable processor, along with associated control software pre-stored on a computer readable storage medium, such as semiconductor or magnetic storage circuits or devices, receives and processes the image(s) captured by the camera to determine the presence of smoke. An (NIR) illuminator, 22, can be used for smoke detection in complete darkness.

In yet another aspect of the invention, a full pan-tilt-zoom camera could be employed to allow for additional pattern targets, which are located at multiple locations of the site. Additional features, such as a feed to a remote display for verification by video can be implemented. The video feed may even be used for purposes beyond just smoke detection, such as security surveillance.

Feed from camera 12 is coupled to processing circuitry 14, which could be implemented with a programmable processor and pre-stored control software. Processing circuitry 14 determines, as explained below, if smoke is present in the region R. Circuitry 14 can include a computer readable storage device wherein various parameters can be stored and accessed by processor 14.

Figure 2:
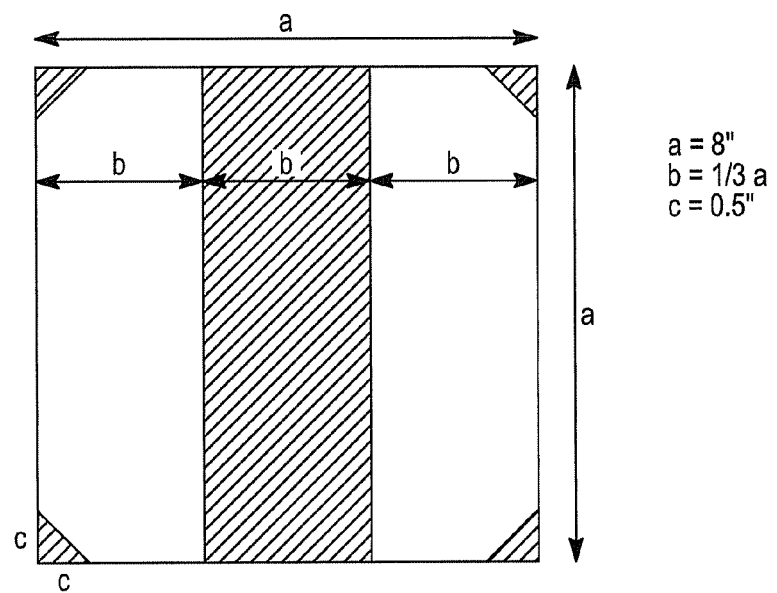
FIG. 2 illustrates a close range target usable in the system of FIG. 1.
Figure 3:
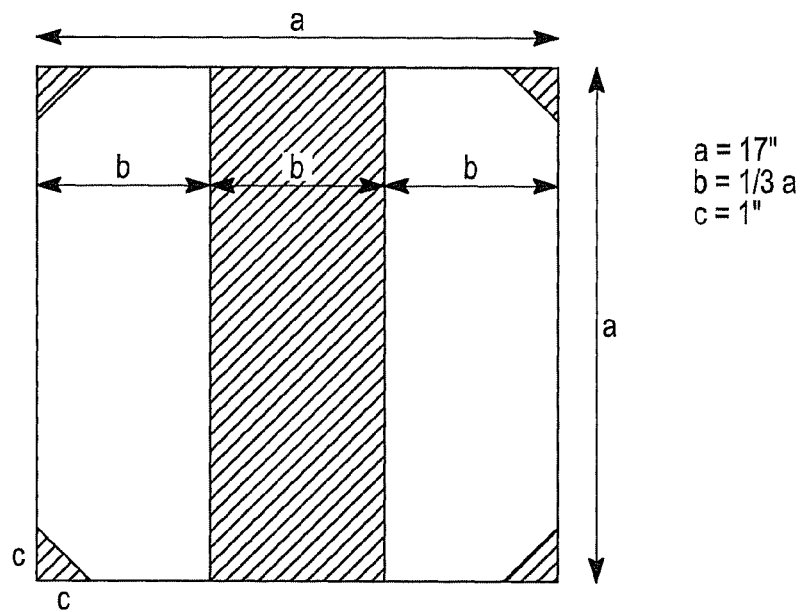
FIG. 3 illustrates a long range target in accordance with the invention.

Two exemplary target designs are discussed below. Other configurations come within the spirit and scope of the invention. FIG. 2 illustrates one which is referred to as close range target, is for smoke detection at a distance less than 50 m. The other, see FIG. 3, referred to as long range target, is for smoke detection at a distance between 50 to 100 m. The target patterns of these two targets are the same; they differ only in size. The objective is to have a common lens, calibration and detection process for all applications.

The triangular shapes at the four corners are for calibration and alignment purposes. The installer adjusts the camera such that the target is within the field of view, preferably close to the center of the image or away from the edge of the image. Then the installer, who responds to a system prompt, needs to identify the four corners of the target in the image.

Figure 4:
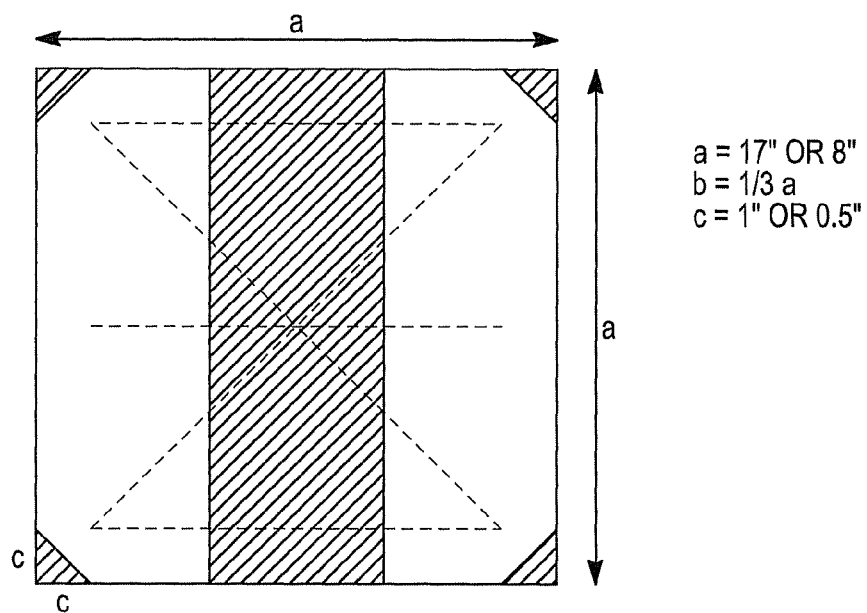
FIG. 4 illustrates aspects of processing intensity profiles in accordance with the invention.

Based on these inputs, the system then generates the reference coordinates of the intensity profiles. Examples of the sections for extracting the intensity profiles are shown as dotted lines in FIG. 4. For example, ten contrast measures can be computed from this example. A robust measurement can be obtained from these ten measures, say, by averaging or finding the median value. Each section can consist of several lines of intensities.

Figure 5:
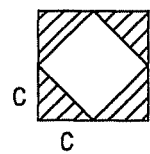
FIG. 5 illustrates an exemplary alignment pattern for reacquiring the target due to target or camera movement.

Furthermore, the system uses these four corners for alignment if the target or the camera moves. The system first creates a reference alignment pattern as shown in FIG. 5. Then the system searches for the same pattern within a search area as outlined in FIG. 12. One can use the entire target as the reference alignment pattern. Using this smaller reference alignment pattern, however, facilitates faster motion detection and target reacquisition.

Figure 6:
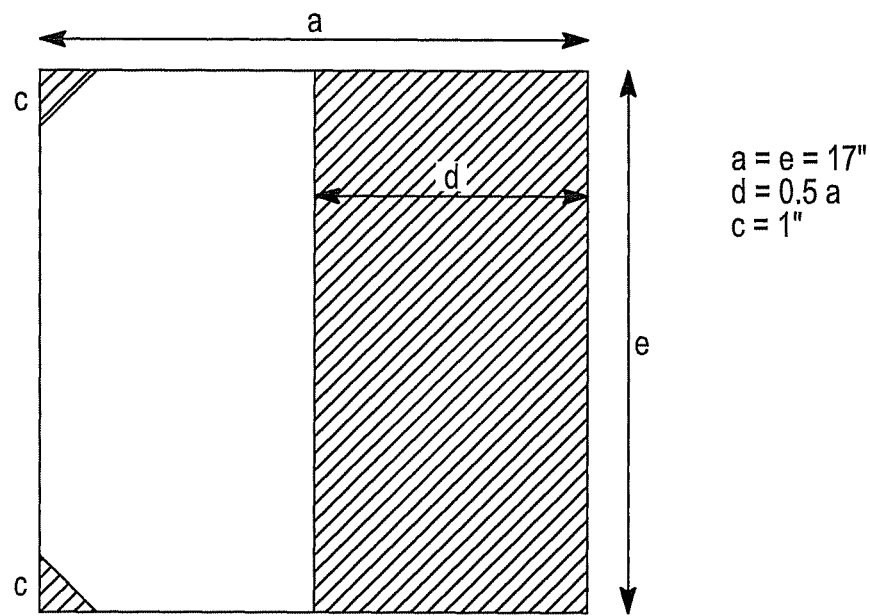
FIG. 6 illustrates an alternate long range target in accordance with the invention.

An alternative target, illustrated in FIG. 6 is designed for a long range (100 m) application. This alternative target provides more pixels per block. Consequently, the numbers of bright and dark values in its intensity profile are larger. Thus, this particular target is more immune to noise, especially for long range applications.

The coating for the dark area of FIG. 6 is preferably an IR absorbent. As a backer material for the target, a board can be used if a screen print can be applied to it.

Figure 7:
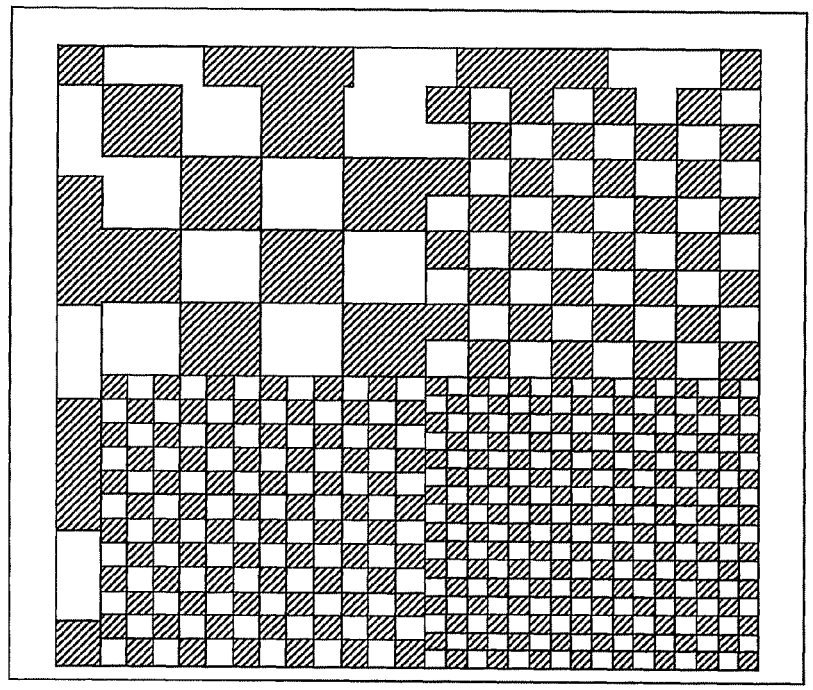
FIG. 7 illustrates an exemplary target under office ambient light in the visible domain.
Figure 8:
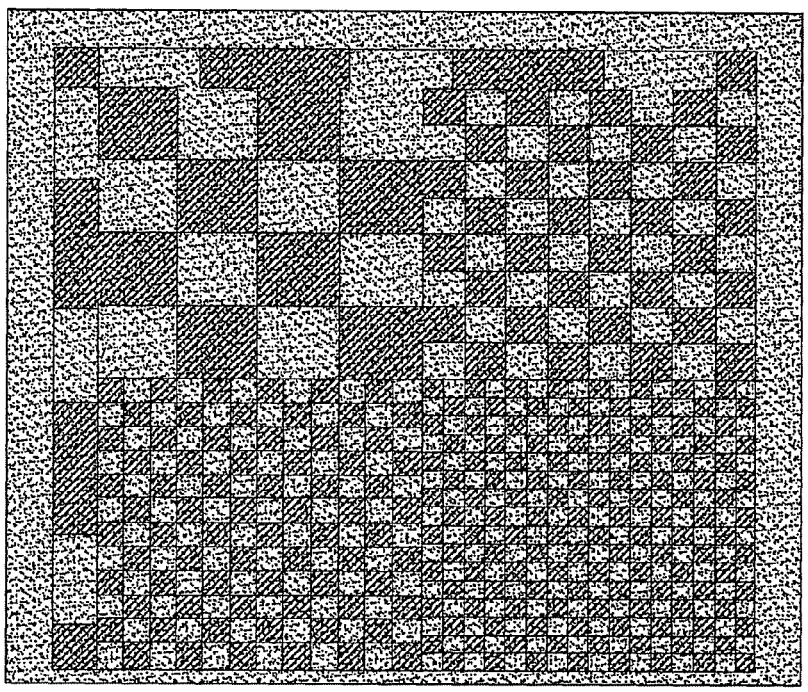
FIG. 8 illustrates an exemplary target under office ambient light as captured with an IR filter on the camera's lens.
Figure 9:
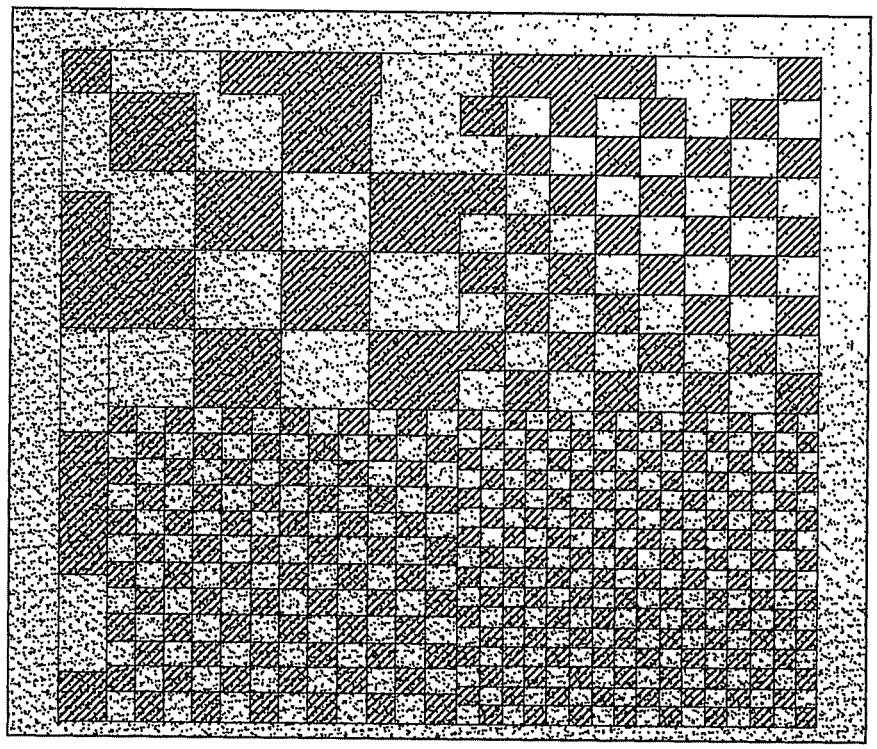
FIG. 9 illustrates an exemplary target under office ambient light and with an IR illuminator, captured with an IR filter on the camera's lens.

The following figures show that the board is reflective in the NIR. FIG. 7 shows the board under office ambient light without the IR filter (i.e., in visible domain). FIG. 8 shows the board under the office ambient light with the IR filter on the lens. The image is significantly darker and noisier. FIG. 9 shows the board under the office light and a 6 LED IR illuminator with the IR filter on the lens. Specular reflection is observed.

Figure 10:
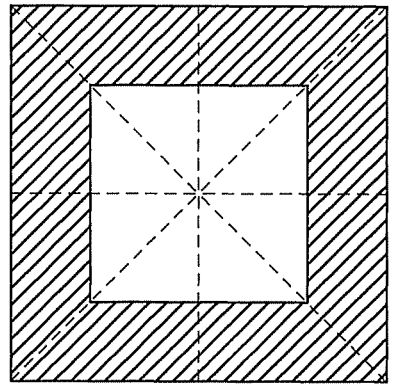
FIG. 10 is a diagram which illustrates another exemplary target pattern and associated processing.
Figure 10:
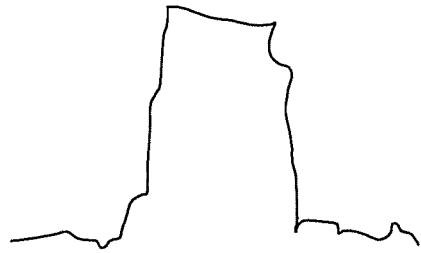

FIG. 10 illustrates another target, configured as a frame. Note that the center of the target is brighter than the border. The construct of this target is further discussed below (in FIGS. 13 and 14.) The dotted line again denotes the sections where intensity profiles are extracted to compute the contrast measures. In addition to using the contrast measure, the average intensity of the bright area can also be computed and used as the smoke detection metric. These two metrics compliment each other.

Figure 11:
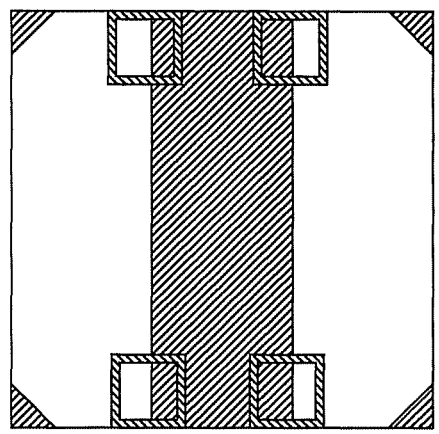
FIG. 11 illustrates an alternate motion tracking mark.
Figure 11:
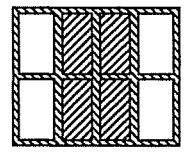

FIG. 11 illustrates an alternate motion tracking mark. When the target is at a far distance, the marking at the corners may not be distinctly visible. In such a case, other demarcation indicia could be used to generate a unique pattern for target reacquisition due to motion. In the illustrated example, the alternate indicia are the small squares. The combined search pattern is illustrated on the right in FIG. 11

Figure 12:
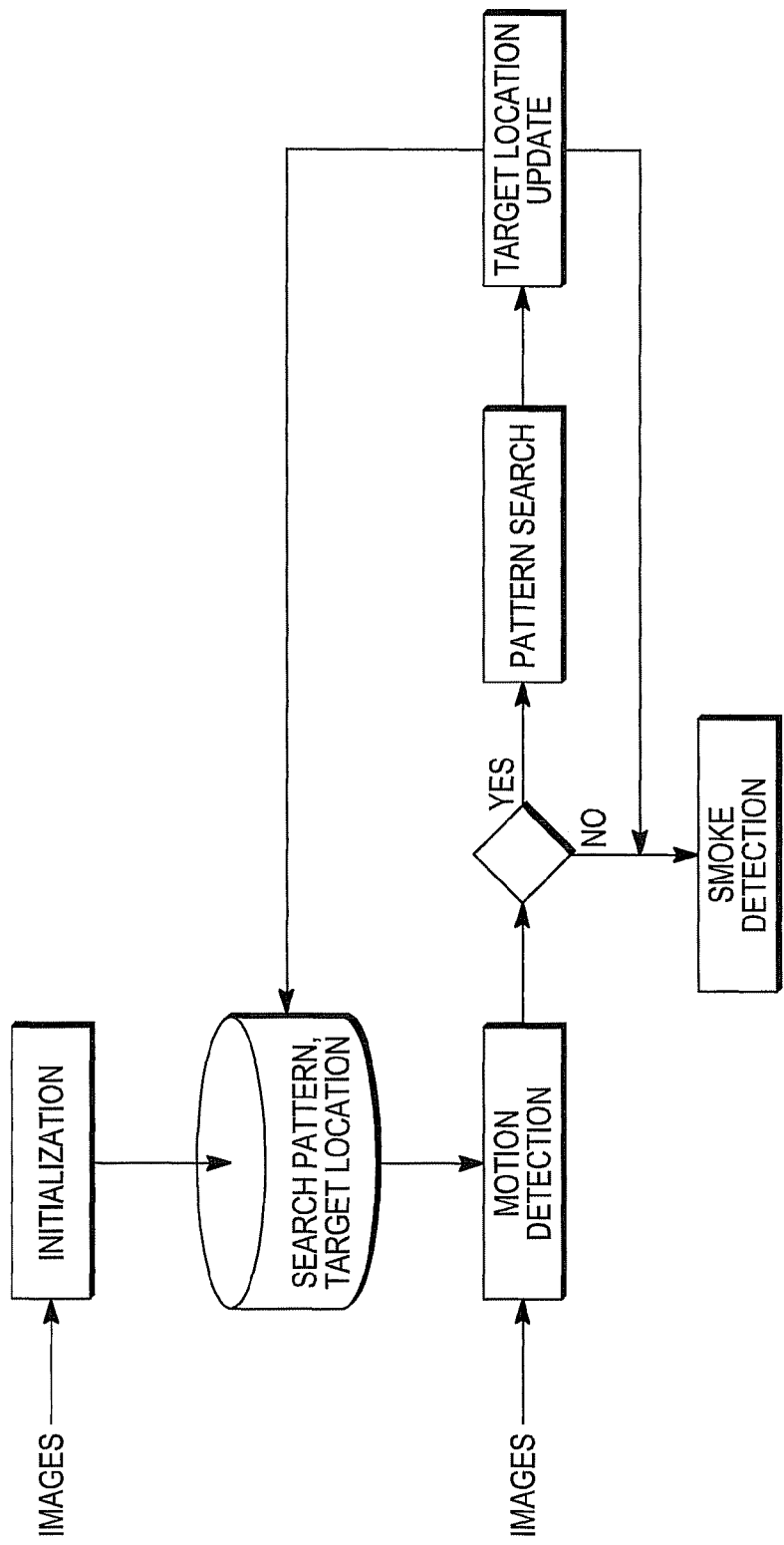
FIG. 12 is a flow diagram of motion detection and reacquisition.

One disadvantage of a beam-based smoke detection is lost of signal due to displacement caused by relative motion of the transmitter and the receiver. This invention circumvents this issue with motion detection and target reacquisition. FIG. 12 illustrates processing relative to target motion detection and reacquisition. The initialization registers the target location in the image, the reference alignment pattern, and the expected motion area where the moved target is searched. During operation, the reference alignment pattern is correlated with the pixels in the expected target location. Target movement is postulated when the correlation is low. Then a set of pixels within the target search area is iteratively selected and correlate with the reference alignment pattern. A high correlation indicates the location of the moved target, which is then updated for subsequent motion detection and smoke detection.

Figure 13:
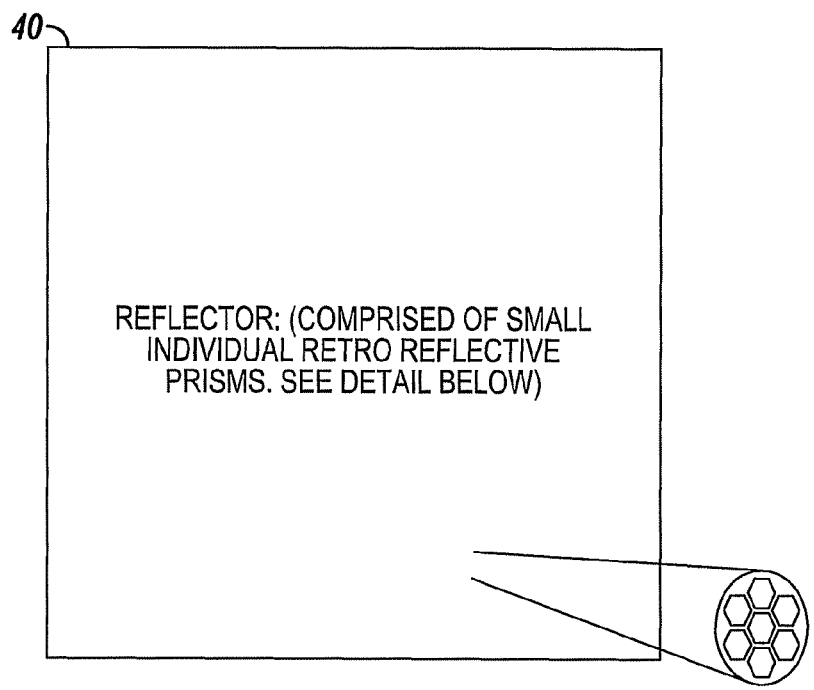
FIG. 13 illustrates aspects of a reflector in accordance with the invention.
Figure 14:
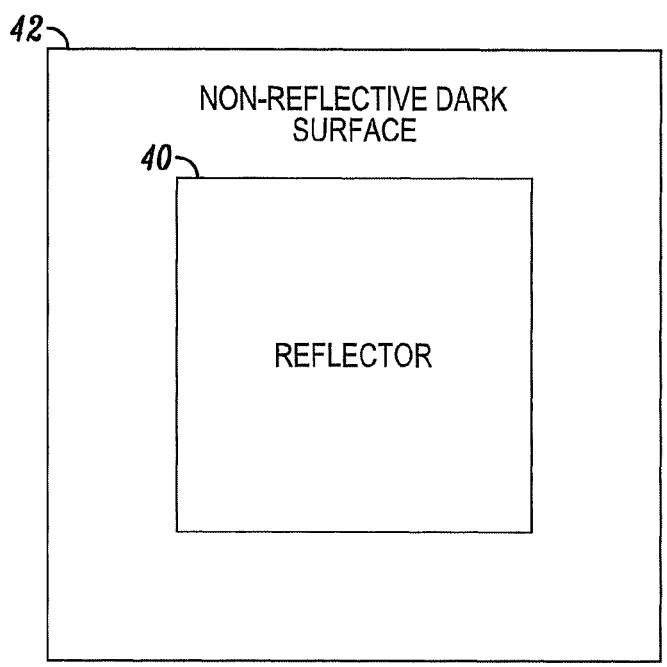
FIG. 14 illustrates additional aspects of a reflector in accordance with the invention.

The bright area of the target should have a positive response to incident radiation, in particular to IR. This is important to long distance application. The illuminator, if mounted on the camera, requires focus and large power to reach the target. The illuminator could be mounted close by or at the target. This installation requires additional power supply at the target area. Hence, if the target response positively, i.e. reflecting most of the incident radiation, the amount of power required for the illuminator would be significantly reduced. FIG. 13 illustrates a reflector 40 which could be formed of small, individual retro reflective prisms. As illustrated in FIG. 14, a target can be constructed with reflector 40 framed by a non-reflective dark surface 42.

Figure 15:
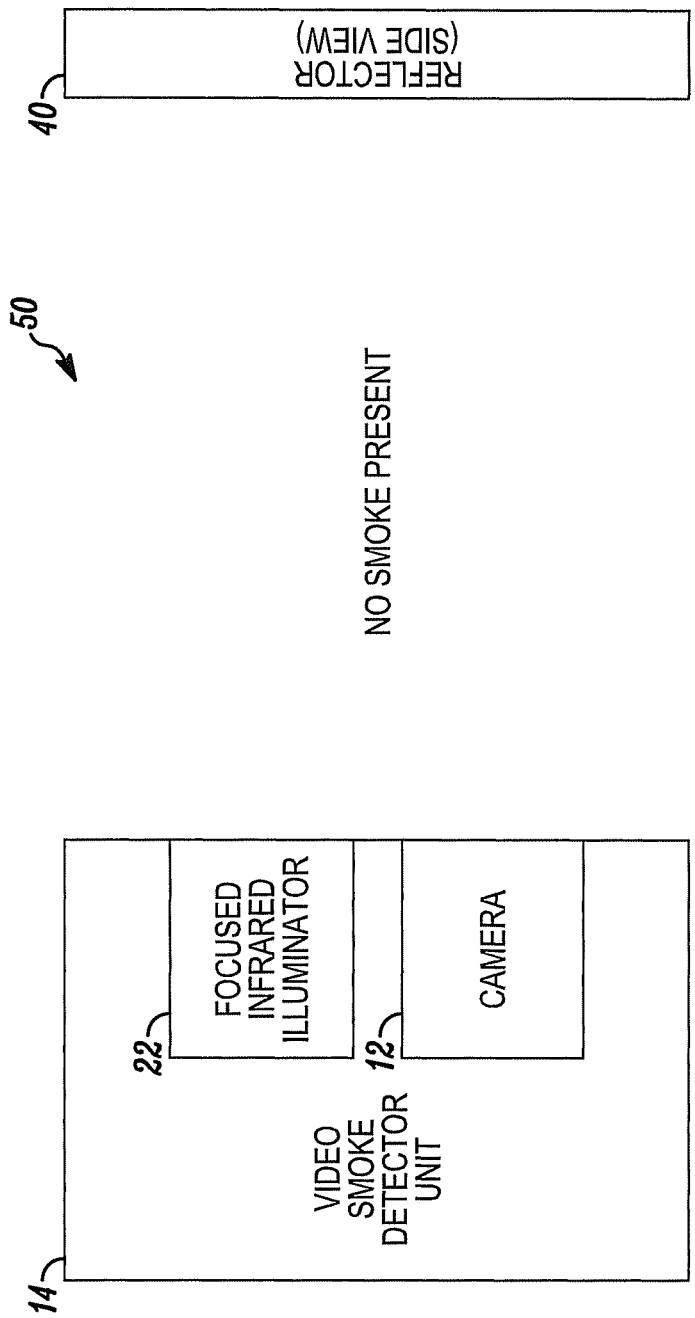
FIG. 15 illustrates a block diagram of a smoke detecting system which incorporates a reflector as in FIG. 14 in a no smoke condition.

FIG. 15 illustrates a system 50 for detecting smoke in accordance with another embodiment of the invention. Components previously discussed have been assigned the same designation numerals as in FIG. 1. FIG. 15, a no smoke present condition results in camera 12 receiving a fully illuminated image of reflector 40 with high contrast between the reflector 40 and surrounding surfaces 42.

Reflectors such as 40 send light directly back to the vicinity of the illuminator 22. The camera 12 receives an image of the reflector 40 as a relative bright light source, even though the illuminator 22 is a relatively low power device.

Figure 16:
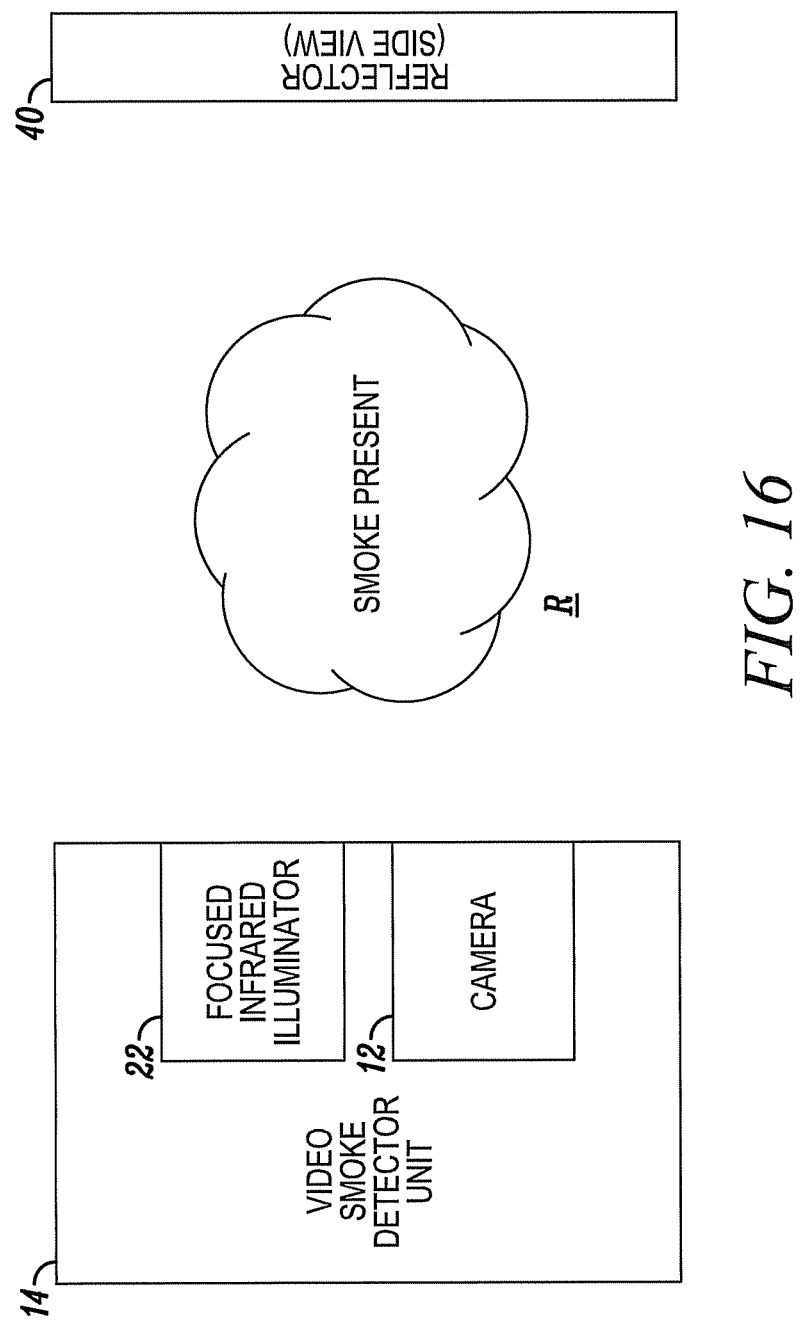
FIG. 16 illustrates the block diagram of FIG. 15 in a condition where smoke is present in the region being monitored.
Figure 17:
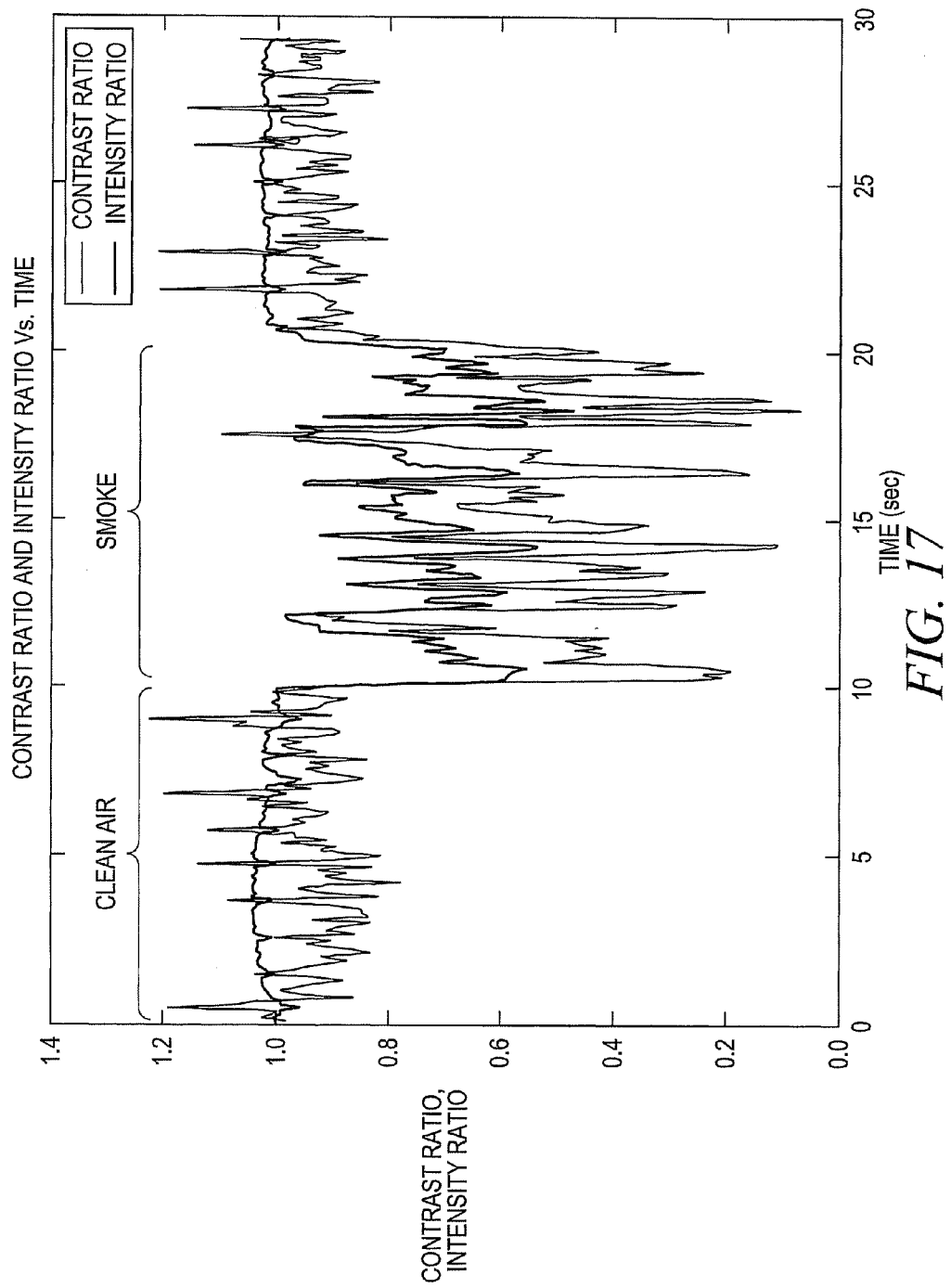
FIG. 17 is a graph illustrating changes in illumination and contrast between no smoke and smoke present conditions.

In FIG. 16, unlike FIG. 15 smoke is present. In this instance the camera 12 detects the reflector 40 with reduced illumination, and reduced contrast between the reflector 40, and surrounding surfaces 42, see graph of FIG. 17, thereby indicating the presence of smoke in the region R being monitored.

Unlike the present invention, known video based smoke detection approaches use flicker, color, or intensity attenuation as the criteria for smoke detection. Flickering depends on the smoke density and combustion state, yielding a very large uncertain dynamic range for smoke detection. Color of the smoke depends on the burning material. Intensity of the smoke is based on the amount of fuel, state of the burning, and the surrounding illumination. These variations result in imprecise smoke detection and produce undesirable false detections. Note that contrast does not depend on the intensity nor the color of the illumination on the target.

Other aspects of the invention also do not require that the test target be perpendicular to the camera. When the target is viewed at an angle off the optical axis of the camera, its image will be distorted. The calibration process estimates the distortion based on the ground truth, and either warps the target or corrects the measured contrast values accordingly if necessary. Any temporal affects in the environment, such as presence of dust, moisture, air turbulence can also be minimized from the calibration. This calibration feature provides a robust smoke detection, very minimal false detection, and diverse installation configurations.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A smoke detector comprising:
a source of a beam of radiant energy;
a target illuminatable by the beam where the target includes at least first and second spaced apart regions which are responsive to the radiant energy as one of a dark patch and a bright patch;
a radiant energy receiver with a field-of-view oriented to include the target; and
processing circuitry coupled to the receiver where the processing circuitry determines a presence of smoke by evaluating at least one of a contrast ratio and an intensity ratio of radiation captured by the receiver and where the target includes at least one indicia or marker usable to establish a location of at least one of the target or the receiver relative to one another.

2. The smoke detector as in claim 1 where the target includes at least one region having negative response to infrared illumination, the at least one region being coated with an infra-red absorbing material.

3. The smoke detector as in claim 1 which includes source activation circuits.

4. The smoke detector as in claim 1 where the target includes a single elongated, dark, region.

5. The smoke detector as in claim 4 where the target includes at least one bounding region with a contrasting color relative to the elongated, dark region.

6. The smoke detector as in claim 5 where the elongated dark region carries an infra-red absorbing dye.

7. The smoke detector as in claim 1 where the target includes at least one region having positive response to infrared illumination, the at least one region including a reflector.

8. The smoke detector as in claim 7 where the target includes a first bright area surrounded by a contrasting region.

9. A smoke detector comprising:
a source of a beam of radiant energy;
a target illuminatable by the beam where the target includes at least first and second spaced apart regions which are responsive to the radiant energy as one of a dark patch and a bright patch;
a radiant energy receiver with a field-of-view oriented to include the target; and
processing circuitry coupled to the receiver where the processing circuitry determines a presence of smoke by evaluating at least one of a contrast ratio and an intensity ratio of radiation captured by the receiver and where the processing circuitry at least intermittently recalibrates a location of the target relative to the receiver.

* * * * *